US009566219B2

(12) United States Patent
Wawiluk et al.

(10) Patent No.: US 9,566,219 B2
(45) Date of Patent: Feb. 14, 2017

(54) TEMPORARY STAIN REPELLENT FOR PREVENTING STAINING OF TEETH

(71) Applicant: Goldspire Group Limited, Causeway Bay (HK)

(72) Inventors: Alex Anthony Wawiluk, Monarch Beach, CA (US); Nicolas Alex Wawiluk, Monarch Beach, CA (US)

(73) Assignee: Goldspire Group Limited, Causeway Bay (HK)

( * ) Notice: Subject to any disclaimer, the term of this patent is extended or adjusted under 35 U.S.C. 154(b) by 0 days.

(21) Appl. No.: 14/405,640

(22) PCT Filed: May 31, 2013

(86) PCT No.: PCT/US2013/043624
§ 371 (c)(1),
(2) Date: Dec. 4, 2014

(87) PCT Pub. No.: WO2013/184510
PCT Pub. Date: Dec. 12, 2013

(65) Prior Publication Data
US 2015/0164753 A1 Jun. 18, 2015

Related U.S. Application Data

(60) Provisional application No. 61/655,691, filed on Jun. 5, 2012.

(51) Int. Cl.
*A61K 8/29* (2006.01)
*A61C 19/06* (2006.01)
*A61Q 11/00* (2006.01)
*A61K 8/85* (2006.01)
*A61K 8/891* (2006.01)
*A61K 8/92* (2006.01)

(52) U.S. Cl.
CPC ............ *A61K 8/29* (2013.01); *A61C 19/066* (2013.01); *A61K 8/85* (2013.01); *A61K 8/891* (2013.01); *A61K 8/922* (2013.01); *A61Q 11/00* (2013.01); *A61K 2800/87* (2013.01)

(58) Field of Classification Search
CPC ....................................... A61K 7/16
USPC ............................................. 424/49
See application file for complete search history.

(56) References Cited

U.S. PATENT DOCUMENTS

| 2002/0006600 A1* | 1/2002 | Cohen ................. 433/217.1 |
| 2004/0146867 A1 | 7/2004 | Slattum et al. |
| 2005/0175552 A1* | 8/2005 | Hoic .................. A61K 8/927 424/49 |
| 2009/0023106 A1 | 1/2009 | Jacobs |
| 2009/0325129 A1 | 12/2009 | Brown et al. |

FOREIGN PATENT DOCUMENTS

| CA | 536 819 A | 2/1957 |
| DE | 197 22 596 A1 | 12/1998 |
| EP | 0 373 688 * | 6/1990 ............... A61K 7/16 |
| EP | 0373688 A2 | 6/1990 |
| EP | 1216681 | 6/2002 |
| JP | H 1171219 | 3/1999 |
| JP | 2001213732 | 8/2001 |
| WO | WO 01/68045 | 9/2001 |

OTHER PUBLICATIONS

Written Opinion for International Application No. PCT/US2013/043624, dated Aug. 30, 2013 in 4 pages.
International Preliminary Report on Patentability for International Application No. PCT/US2013/043624, dated Dec. 9, 2014 in 5 pages.
International Search Report in International Application No. PCT/US2013/043624, mailed Sep. 12, 2013 in 3 pages.
Anonymous, "Castor oil is wonderful", Jun. 5, 2011 URL: http://www.curezone.org/forums/am.asp?i=848295 [retrieved on Nov. 11, 2015].
Extended Search Report for Application No. 13800151.6 dated Nov. 25, 2015 in 9 pages.

* cited by examiner

*Primary Examiner* — Walter Webb
(74) *Attorney, Agent, or Firm* — Knobbe Martens Olson & Bear, LLP

(57) ABSTRACT

Methods, compositions, and products maintain white teeth or prolong the effects of teeth whitening by preventing staining of teeth via a temporary stain repellent. The temporary stain repellent can include a food-grade silicone compound configured to temporarily form a protective layer over teeth or fill the pores of the teeth before and during the consumption of pigmented foods and/or drinks post-teeth whitening.

18 Claims, No Drawings

TEMPORARY STAIN REPELLENT FOR PREVENTING STAINING OF TEETH

BACKGROUND

Field

Embodiments relate to the field of dental care, and, in particular, to methods, compositions, and products for maintaining and prolonging the effects of teeth whitening as well as for maintaining and prolonging the effects of clean naturally white teeth by preventing staining of teeth via a temporary stain repellent.

Description of the Related Art

The benefits of clean white teeth are now recognized by most of the public. People with white teeth are going to great lengths to maintain the white appearance of their teeth while others are spending a considerable amount of money to whiten their teeth, a procedure done by a dentist or hygienist or by applying teeth whitening materials that are sold in the retail market today. With the development of new technologies, various teeth whitening products and procedures are widely available to whiten stained teeth. However, immediately after using such whitening products and procedures, teeth become dehydrated, more porous, and therefore more prone to staining. Susceptibility to staining of teeth can last for several days, or weeks in some cases, after whitening. Accordingly, dental professionals and/or instructions on teeth whitening products generally advise patients and users to abstain from consuming pigmented food and drinks in general and particularly after whitening. Common acidic foods and beverages such as wine, yogurt, and orange juice can also temporarily demineralize or etch the surface of the enamel, thereby also making teeth more susceptible to staining.

SUMMARY

Advancements in technology make it possible to maintain and/or prolong the effects of white teeth or teeth whitening products and/or procedures. In some embodiments, a method of prolonging the white color of teeth or the effects of a teeth whitening product or procedure comprises applying a temporary stain repellent to teeth subjected to anticipated teeth staining activities or pigment depositing activities immediately before said activities, thereby forming a protective seal over the teeth and engaging in said activities, wherein the protective seal prevents the teeth staining activities or pigment depositing activities from directly accessing the teeth, thereby substantially preventing staining of the teeth. In certain embodiments, the temporary stain repellent in the above method is applied to teeth subjected to a teeth whitening product or procedure within about the preceding year, within about six months, within about five months, within about four months, within about three months, within about eight weeks, within about seven weeks, within about six weeks, within about five weeks, within about four weeks, within about three weeks, within about two weeks, within about one week, within about six days, within about five days, within about four days, within about three days, within about two days, within about one day, within about twelve hours, within about six hours, within about four hours, within about two hours, or within about zero hours. In certain embodiments, the anticipated teeth staining activities or pigment depositing activities in the above method comprises consuming a pigmented food or drink.

In certain embodiments, the temporary stain repellent in the above method comprises food-grade silicone. In certain embodiments, the temporary stain repellent in the above method comprises castor oil. In certain embodiments, the temporary stain repellent in the above method comprises liquid polyester. In certain embodiments, the temporary stain repellent in the above method comprises a gel. In certain embodiments, the temporary stain repellent in the above method comprises a liquid. In certain embodiments, the temporary stain repellent in the above method comprises a solid. In certain embodiments, applying the temporary stain repellent comprises filling a tray with the temporary stain repellent and submerging teeth in the tray filled with the temporary stain repellent for about one minute. In certain embodiments, the tray in the above method is pre-formed. In certain embodiments, the tray in the above method comprises beeswax or similar non-toxic material and is configured to be instantly molded to fit or substantially fit teeth before each use. In certain embodiments, the temporary stain repellent in the above method is substantially flavorless. In certain embodiments, the temporary stain repellent in the above method comprises titanium dioxide.

In certain embodiments, the temporary stain repellent in the above method is configured to be applied with a brush. In certain embodiments, the temporary stain repellent in the above method is configured to be applied with a felt-tipped applicator. In certain embodiments, the temporary stain repellent in the above method is configured to be applied as a roll-on material similar to lip stick. In certain embodiments, the temporary stain repellent in the above method is configured to be applied as a mouth rinse. In certain embodiments, the temporary stain repellent in the above method is configured to be applied with a finger of a user. In certain embodiments, the temporary stain repellent in the above method is configured to be applied with a stain repellent saturated tissue, gauze or pad.

In certain embodiments, a system for prolonging the white color of teeth or the effects of a teeth whitening product or procedure, comprises a tray adapted to receive a set of upper and/or lower teeth of a user, and a temporary stain repellent adapted to form a protective seal over the teeth prior to the user engaging in pigment-depositing activity.

In some embodiments, the temporary stain repellent of the aforementioned system comprises food-grade silicone. In other embodiments, the temporary stain repellent of the aforementioned system can comprise castor oil. In some embodiment, the temporary stain repellent of the aforementioned system comprises liquid polyester. In further embodiments, the temporary stain repellent of the aforementioned system comprises a gel, liquid, or solid.

In certain embodiments, the tray of the aforementioned system is pre-formed. In other embodiments, the tray of the aforementioned system comprises beeswax that can be instantly molded to fit or substantially fit teeth before each use. In some embodiments, the temporary stain repellent of the aforementioned system is substantially flavorless. In some embodiments, the temporary stain repellent of the aforementioned system further comprises titanium dioxide.

For purposes of this summary, certain aspects, advantages, and novel features are described herein. It is to be understood that not necessarily all such advantages may be achieved in accordance with any particular embodiment. Thus, for example, those skilled in the art will recognize that the invention may be embodied or carried out in a manner that achieves one advantage or group of advantages as taught herein without necessarily achieving other advantages as may be taught or suggested herein.

DETAILED DESCRIPTION OF THE EMBODIMENTS

Embodiments of the invention will now be described. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

Teeth are stained for various reasons. For example, teeth can become darker with age as the enamel becomes thinner. Teeth are also stained by pigments found in various foods and drinks, tobacco, cigarette or cigar smoke, and antibiotics such as tetracycline, dental antiseptics such as chlorohexadine, and fluorides such as stannous fluoride, among others. Some examples of pigmented foods and drinks that are likely to stain teeth include coffee, tea, red wine, cola, sports drinks, berries, dark sauces, sweets, ketchup, soy sauce, dark soda, and dark fruit juice, among others.

With the advancement of teeth whitening technology, various teeth bleaching and/or whitening procedures and products are now widely available. As used herein, the terms "teeth whitening" and "teeth bleaching" may be used interchangeably. For example, there are brushing solutions, strips, pens, gels, light-accelerated procedures, and overnight trays, among others. Such procedures and products provide an after-the-fact solution to whiten teeth that have already been stained. Some teeth whitening products whiten teeth by mechanically abrading the stains appearing on the enamel layer. Other teeth whitening products penetrate through the porous enamel layer and whiten or oxidize stain deposits in the dentin. However, the downside to many of these teeth whitening products and/or procedures is that immediately after whitening, teeth become more porous, more sensitive, and highly susceptible to staining. Susceptibility to staining can peak in the first 48 hours post-whitening and can last for two weeks or more. Thus, prevention of stains during this initial period after tooth whitening can be particularly important. Also, consuming low pH food and beverages also makes the teeth more susceptible to staining. Nevertheless, it is also desirable to maintain the whiteness of teeth for a longer period of time after this initial whitening period or at any other time. Accordingly, the techniques described in connection with embodiments described herein are typically applied right after teeth whitening or during any period of time where extra teeth protection is desired. For example, the techniques described in connection with embodiments described herein can be applied when teeth whitening has been conducted within about the preceding year, within about six months, within about five months, within about four months, within about three months, within about eight weeks, within about seven weeks, within about six weeks, within about five weeks, within about four weeks, within about three weeks, within about two weeks, within about one week, within about six days, within about five days, within about four days, within about three days, within about two days, within about one day, within about twelve hours, within about six hours, within about four hours, within about two hours, or within about zero hours.

Despite the development and widespread use of various teeth whitening products and procedures for over 20 years, issues related to susceptibility to staining of teeth in general and post-whitening have not been adequately addressed. Rather, dental professionals and instructions on various teeth whitening products simply advise patients and users to abstain from consuming pigmented food and drinks in general and particularly after whitening. This is inconvenient, to say the least, for users of teeth whitening products and procedures. Moreover, it is only a matter of time until a patient or user consumes pigmented foods and/or drinks, re-staining teeth after whitening. In other words, teeth whitening products and procedures are effective only for so long as the user continues to refrain from consuming pigmented foods and/or drinks. The only other alternative that a dentist offers the patient is additional teeth whitening materials in order to "touch-up" newly stained teeth.

As an alternative to simply refraining from consuming pigmented foods and/or drinks, embodiments disclosed herein provide easy and convenient methods, compositions, and products to maintain and prolong the effects of teeth whitening while permitting consumption of pigmented foods and/or drinks after whitening. Further, contrary to teeth whitening products, embodiments disclosed herein provide before-the-fact solutions to prevent staining of teeth.

Overview of Temporary Stain Repellent

In an embodiment, a temporary stain repellent as described herein can be applied to teeth before consuming pigmented foods and/or drinks to prevent staining. In some embodiments, once the temporary stain repellent is applied, a temporary seal forms around the user's teeth or in the pores of the teeth to prevent staining materials or compositions from staining or being absorbed by the enamel while the user consumes pigmented foods and/or drinks. Accordingly, a user can safely consume pigmented foods and/or drinks even immediately after whitening with the help of the temporary stain repellent.

In some embodiments, the temporary stain repellent can be applied to teeth before consuming pigmented foods and/or drinks or engaging in other teeth staining activities to maintain and prolong the effects of white teeth and/or teeth whitening. In certain embodiments, the temporary stain repellent can be applied before engaging in teeth staining activities after whitening. For example, the temporary stain repellent can be applied to teeth subjected to one or more various teeth whitening products or procedures described above within any of the time periods after whitening described above, i.e. within about the preceding year, within about six months, within about five months, within about four months, within about three months, within about eight weeks, within about seven weeks, within about six weeks, within about five weeks, within about four weeks, within about three weeks, within about two weeks, within about one week, within about six days, within about five days, within about four days, within about three days, within about forty-eight hours, within about twenty-four hours, within about twelve hours, within about six hours, within about four hours, within about two hours, within about zero hours, or within about any other time period.

It is typically desired that the stain preventative effect of the protective seal last for a period of time sufficient to preventing staining during the immediate consumption of staining foods or beverages. Thus, in some embodiments, the protective seal formed by the temporary stain repellent will preferably last for a period of at least about 3 minutes, at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 1 hour, at least about 90 minutes, at least about 2 hours, at least about 150 minutes, or at least about 3 hours. In some embodiments, the protective seal formed by the temporary stain repellent can last for a period as long as at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 1 hour, at least about 90 minutes, at least about 2 hours, at least about 150 minutes, at least about 3 hours, at least about 210 minutes, at least about 4 hours, at least about 270 minutes, at least about 5 hours, at least about 330 minutes, at least about 6 hours, at least about 390 minutes, at least about 7 hours, at least about 450 minutes, at least about 8 hours, at least about 510 minutes, at least about 9 hours, at least about 570 minutes, at least about 10 hours, at least about 630 minutes, at least about 11 hours, at least about 690 minutes, at least about 12 hours, at least about 24 hours, at least about 48 hours, at least about 72 hours or any other time period. Within this time period, the seal formed by the temporary stain repellent wears off, returning teeth to their natural state such that normal physiological functions of the teeth are restored.

In some embodiments, use of the temporary staining repellent before consuming pigmented foods and/or drinks reduces the degree of staining of teeth by at least about 99% compared to when consuming the same foods and/or drinks without using the temporary staining repellent. In other embodiments, the temporary staining repellent reduces the degree of staining of teeth by at least about 98%, at least about 97%, at least about 96%, at least about 95%, at least about 94%, at least about 93%, at least about 92%, at least about 91%, at least about 90%, at least about 85%, at least about 80%, a at least bout 75%, at least about 70%, at least about 65%, at least about 60%, at least about 55%, at least about 50%, about 45%, at least about 40%, at least about 35%, at least about 30%, at least about 25%, about 20%, at least about 15%, at least about 10%, at least about 5% or any other percentage.

Product Form and Application

In some embodiments, the temporary stain repellent is in the form of a gel, paste, or solid. Once applied to a user's teeth, the gel, paste, or solid can be applied to form a sealant covering the teeth and/or pores to prevent staining foods and drinks from entering the teeth. In some embodiments, the gel, paste, or solid must be in contact with a user's teeth for a certain period of time in order for the gel, paste, or solid to form a protective layer over the teeth and/or pores. For example, the time required for the protective seal to form can be at least about 1 second, at least about 5 seconds, at least about 10 seconds, at least about 15 seconds, at least about 20 seconds, at least about 25 seconds, at least about 30 seconds, at least about 1 minute, at least about 1 minute and 30 seconds, at least about 2 minutes, at least about 2 minutes and 30 seconds, at least about 3 minutes, at least about 3 minutes and 30 seconds, at least about 4 minutes, at least about 4 minutes and 30 seconds, at least about 5 minutes, or any other period of time.

In some embodiments, the gel or paste is configured to be used in conjunction with a tray. For example, a user can fill a tray with the gel, paste, or solid and fit the tray inside the user's mouth in a manner such that the user's teeth are submerged in the gel or paste. By using a tray, the gel, paste, or solid can form a protective seal that covers substantially all surfaces of the user's teeth, including the buccal, lingual, occlusal, distal, and/or mesial surfaces. Further, by using a tray, protective seals can be substantially prevented from forming over other undesirable oral areas, such as the user's tongue and/or gums.

In some embodiments, the tray to be used in conjunction with the temporary stain repellent is pre-formed. For example, the tray can be pre-formed trays that are available for sale either in conjunction with or separate from the temporary stain repellent. Alternatively, a user can obtain the tray from a dentist or other dental professional. The dentist or other dental professional may have performed a teeth whitening procedure for the user. In other embodiments, the tray is not pre-formed but can be molded before using the temporary stain repellent. For example, a tray can be molded to fit or substantially fit the user's teeth before applying the temporary stain repellent. In some embodiments, the tray can be molded instantly to fit or substantially fit the user's teeth. In certain embodiments, the moldable tray comprises beeswax or similar non-toxic material. A moldable tray can be sold in conjunction with or separate from the temporary stain repellent.

In some embodiments, the gel, paste, or solid is configured to be used in conjunction with an apparatus for painting the gel or paste over teeth. For example, the apparatus can include but is not limited to a brush, tissue, gauze, pad, felt-tipped applicator, or finger, among other possible options. In certain embodiments, a user can place some of the gel, paste, or solid on the apparatus and apply the gel, paste, or solid to the user's teeth manually. By using such apparatus, the user can select which teeth or surfaces thereof to cover with a protective layer. For example, a user can use an apparatus to apply the gel, paste, or solid only on the buccal surfaces and not the lingual, occlusal, distal, or mesial surfaces. This way, a protective layer or seal will form only over the buccal surfaces and not over other surfaces of the teeth or other oral areas such as the tongue. In some embodiments, an appropriate apparatus of the sort described above is sold in conjunction with or separate from the temporary stain repellent. For example, a container comprising the temporary stain repellent can further comprise a brush, felt-tipped applicator, or other apparatus that allows a user to directly paint the temporary stain repellent on the user's teeth.

In some embodiments, the temporary stain repellent is substantially solid. For example, the temporary stain repellent can be of a form similar to that of lipstick. In such embodiments, a user can directly apply the temporary stain repellent to surfaces of teeth to paint the temporary stain repellent over teeth. In some embodiments, the temporary stain repellent comprises one or more types of wax to provide the solid structure. For example, the temporary stain repellent can comprise beeswax, ozokerite, candelilla wax, carnauba wax, or any other suitable wax or other non-toxic composition that can provide a substantially solid structure. In some embodiments, the lipstick-form temporary stain repellent comprises a pointed end that allows a user to reach mesial or distal surfaces in between teeth or at least portions thereof. Further, as described above, the lipstick-form temporary stain repellent allows the user to apply the temporary stain repellent only on certain surfaces of teeth without covering other oral areas such as the tongue.

In some embodiments, the temporary stain repellent is in the form of a sheet(s) or strip(s). A user can place the sheet or strip over the user's teeth for a certain period of time and subsequently remove it to coat the user's teeth with the temporary stain repellent. In some embodiments, the strip may be left on for a given period of time. A single container or package can comprise one or more of such sheets or strips. In some embodiments, a single sheet or strip is roughly the size of the buccal surface of a single tooth. In other embodiments, a single sheet or strip is large enough to substantially cover the buccal surface of a single tooth and portions of the distal, mesial, occlusal, and lingual surfaces of the same tooth. In other embodiments, a single sheet or strip is large enough to cover the buccal surfaces of more than one tooth. By using a sheet-form temporary stain repellent, a user can prevent applying the temporary stain repellent over the user's tongue.

In some embodiments, the temporary stain repellent is liquid. For example, the temporary stain repellent can be configured to be used as a mouthwash. In such embodiments, a user can swish and/or swirl the mouthwash inside the user's mouth for a period of time that is sufficient for the temporary stain repellent to attach and form a protective layer over the user's teeth.

In some embodiments, the temporary stain repellent is in the form of a spray. In such embodiments, a user can spray the temporary stain repellent over the user's teeth. The temporary stain repellent sprayed onto the user's teeth can form a protective seal. In some embodiments, a container comprising the temporary stain repellent can further comprise a spray head that allows a user to spray the temporary stain repellent. A user can use the spray form temporary stain repellent to prevent application of the temporary stain repellent over the user's tongue.

In the embodiments described above, the time required for the protective seal to form can be as short as within about 1 second, within about 5 seconds, within about 10 seconds, within about 15 seconds, within about 20 seconds, within about 25 seconds, within about 30 seconds, within about 1 minute, within about 1 minute and 30 seconds, within about 2 minutes, within about 2 minutes and 30 seconds, within about 3 minutes, within about 3 minutes and 30 seconds, within about 4 minutes, within about 4 minutes and 30 seconds, within about 5 minutes, or any other period of time to as long as at least about 2 seconds, at least 5 seconds, at least about 10 seconds, at least about 15 seconds, at least about 20 seconds, at least about 25 seconds, at least about 30 seconds, at least about 1 minute, at least about 1 minute and 30 seconds, at least about 2 minutes, at least about 2 minutes and 30 seconds, at least about 3 minutes, at least about 3 minutes and 30 seconds, at least about 4 minutes, at least about 4 minutes and 30 seconds, at least about 5 minutes, at least about 10 minutes, at least about 20 minutes, at least about 30 minutes, at least as long as about one hour, or any other period of time.

Composition

In an embodiment, the temporary stain repellent comprises a food-grade sealant which forms the protective seal or layer. The food-grade sealant can be any food-grade material or composition that can form a temporary protective layer over teeth. For example, the food-grade sealant can be any hydrophobic food-grade sealant or any combinations thereof. In some embodiments, the sealant is a food-grade silicone, including but not limited to organopolysiloxanes, silicone oils, amino alkyl silicone, or any other foodgrade silicone compound. Some suitable silicone oils can include dimethylpolysiloxane. British Patent No. 789, 851, British Patent No. 686,429, Canadian Patent No. 536, 819, and U.S. Pat. No. 5,422,098 are incorporated herein by reference.

In certain embodiments, the sealant is food-grade liquid polyester. In other embodiments, the sealant is food-grade Caster oil.

In some embodiments, the temporary stain repellent can comprise active and/or inactive ingredients, including but not limited to one or more flavoring agents and/or coloring agents. In some embodiments, remineralizaing agents such as hydroxyapatite may be used. In further embodiments, the temporary stain repellant can comprise ingredients that protect teeth from the effects of acid. In some embodiments, the temporary stain repellant can comprise ingredients that protect teeth from demineralization. In certain embodiments, the temporary stain repellent comprises a mild flavoring agent that does not affect the taste of food and/or drinks the user consumes after applying the temporary stain repellent. In some embodiments, the temporary stain repellent does not comprise any flavoring agent. In certain embodiments, the temporary stain repellent is substantially flavorless or has a flavor.

In some embodiments, the temporary stain repellent does not comprise any coloring agents or strong coloring agents. For example, the temporary stain repellent can be clear or substantially clear in color or can be white. In other embodiments, the temporary stain repellent is substantially colorless. In some embodiments, the temporary stain repellent comprises titanium dioxide.

Although the embodiments of the inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above.

What is claimed is:

1. A method of maintaining and prolonging the effects of teeth bleaching selected from a group consisting of mechanically abrading stains on an enamel layer of teeth and penetrating through the enamel layer to whiten stain deposits in dentin of the teeth, the method comprising:
   forming a protective seal that lasts for a period of time of at least about 10 minutes to as long as about 24 hours over teeth bleached by said teeth bleaching within three days of said teeth bleaching, the protective seal formed by applying a temporary stain repellent to the teeth before applying a pigment deposit to the teeth; and
   applying the pigment deposit to the teeth during the period, wherein the protective seal prevents the pigment deposit from directly accessing the teeth, thereby substantially preventing staining of the teeth during the period,
   wherein the protective seal wears off during the period.

2. The method of claim 1, wherein the pigment deposit comprises a pigmented food or drink.

3. The method of claim 1, wherein the temporary stain repellent comprises food-grade silicone.

4. The method of claim 1, wherein the temporary stain repellent comprises castor oil.

5. The method of claim 1, wherein the temporary stain repellent comprises liquid polyester.

6. The method of claim 1, wherein the temporary stain repellent comprises a gel, liquid, spray or solid.

7. The method of claim 1, wherein applying the temporary stain repellent comprises filling a tray with the temporary stain repellent and submerging the teeth in the tray filled with the temporary stain repellent for about one minute.

8. The method of claim 7, wherein the tray is pre-formed.

9. The method of claim 7, wherein the tray comprises beeswax and is instantly molded to fit or substantially fit the teeth before each use.

10. The method of claim 1, wherein the temporary stain repellent further comprises titanium dioxide.

11. The method of claim 3, wherein the food grade silicone is selected from the group consisting of silicone oils, organopolysiloxanes, or amino alkyl silicone.

12. The method of claim 1, wherein the protective seal is formed in less than about 2 minutes.

13. The method of claim 1, wherein the temporary stain repellent is in a solid lipstick form before being applied to the teeth.

14. The method of claim 1, wherein the protective seal reduces staining of teeth by at least about 90%.

15. The method of claim 1, wherein the protective seal reduces staining of teeth by at least about 95%.

16. The method of claim 1, wherein the protective seal is formed over substantially all surfaces of the teeth.

17. The method of claim 1, wherein the protective seal is only formed on the teeth.

18. The method of claim 1, wherein the protective seal is formed only over buccal surfaces of the teeth.

* * * * *

UNITED STATES PATENT AND TRADEMARK OFFICE
CERTIFICATE OF CORRECTION

PATENT NO. : 9,566,219 B2  
APPLICATION NO. : 14/405640  
DATED : February 14, 2017  
INVENTOR(S) : Alex Anthony Wawiluk Page 1 of 1

It is certified that error appears in the above-identified patent and that said Letters Patent is hereby corrected as shown below:

In the Specification

In Column 3 at Lines 21-22, Change "chlorohexadine," to --chlorhexidine,--.

In Column 8 at Line 7, Change "remineralizaing" to --remineralizing--.

In the Claims

In Column 9 at Line 19 (approx.), In Claim 10, after "repellent" delete "further".

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*